United States Patent [19]

Wentworth et al.

[11] Patent Number: 5,394,091

[45] Date of Patent: Feb. 28, 1995

[54] SYSTEM FOR DETECTING COMPOUNDS IN A GASEOUS SAMPLE BY MEASURING PHOTOIONIZATION AND ELECTRON CAPTURE INDUCED BY SPARK EXCITATION OF HELIUM

[76] Inventors: Wayne E. Wentworth, Chemistry Dept., University of Houston, Houston, Tex. 77204-5641; Stanley D. Stearns, 1201 Archley Dr., Houston, Tex. 77055

[21] Appl. No.: 201,469

[22] Filed: Feb. 25, 1994

Related U.S. Application Data

[63] Continuation-in-part of Ser. No. 956,632, Oct. 5, 1992, Pat. No. 5,317,271, which is a continuation-in-part of Ser. No. 662,149, Feb. 28, 1991, Pat. No. 5,153,519.

[51] Int. Cl.$^6$ .................... G01N 27/62; G01N 27/68
[52] U.S. Cl. .................... 324/464; 324/455; 73/28.02
[58] Field of Search ............ 324/123 R, 71.4, 449, 324/450, 452, 445, 464; 73/28.02, 23.35; 436/153; 313/231.41, 231.71; 315/111.01, 111.91; 250/379, 385.2

[56] References Cited

U.S. PATENT DOCUMENTS

| | | | |
|---|---|---|---|
| 3,540,851 | 11/1970 | Vree et al. | 324/464 X |
| 3,679,973 | 7/1972 | Smith, Jr. et al. | 324/464 X |
| 4,724,394 | 2/1988 | Langer et al. | 324/464 |
| 4,851,683 | 7/1989 | Yang et al. | 250/339 |
| 5,153,519 | 10/1992 | Wentworth et al. | 324/464 |
| 5,317,271 | 5/1994 | Wentworth et al. | 324/464 |

*Primary Examiner*—Gerard R. Strecker
*Assistant Examiner*—Diep Do
*Attorney, Agent, or Firm*—Cunn & Kuffner

[57] ABSTRACT

A pulsed discharge helium ionization detector set forth and comprises an elongate cylindrical body having an axially flow path. A helium source is connected to deliver helium flowing along this path. At some location in the helium flow path, transversely positioned, facing electrodes are located. When provided with pulses discharged across the helium flow path wherein the discharge is either monopolar or bipolar pulses, the spark interacts with the helium to create photon ionization. Downstream within view of the spark, a counter flow sample injection tube is positioned to deliver samples at a reduced flow rate. The sample is swept back along the helium flow path past a pair of electrode rings spaced along the flow path. The interaction of the photon ionization with the sample creates a current which can be detected by an electrometer across the two terminals.

11 Claims, 1 Drawing Sheet

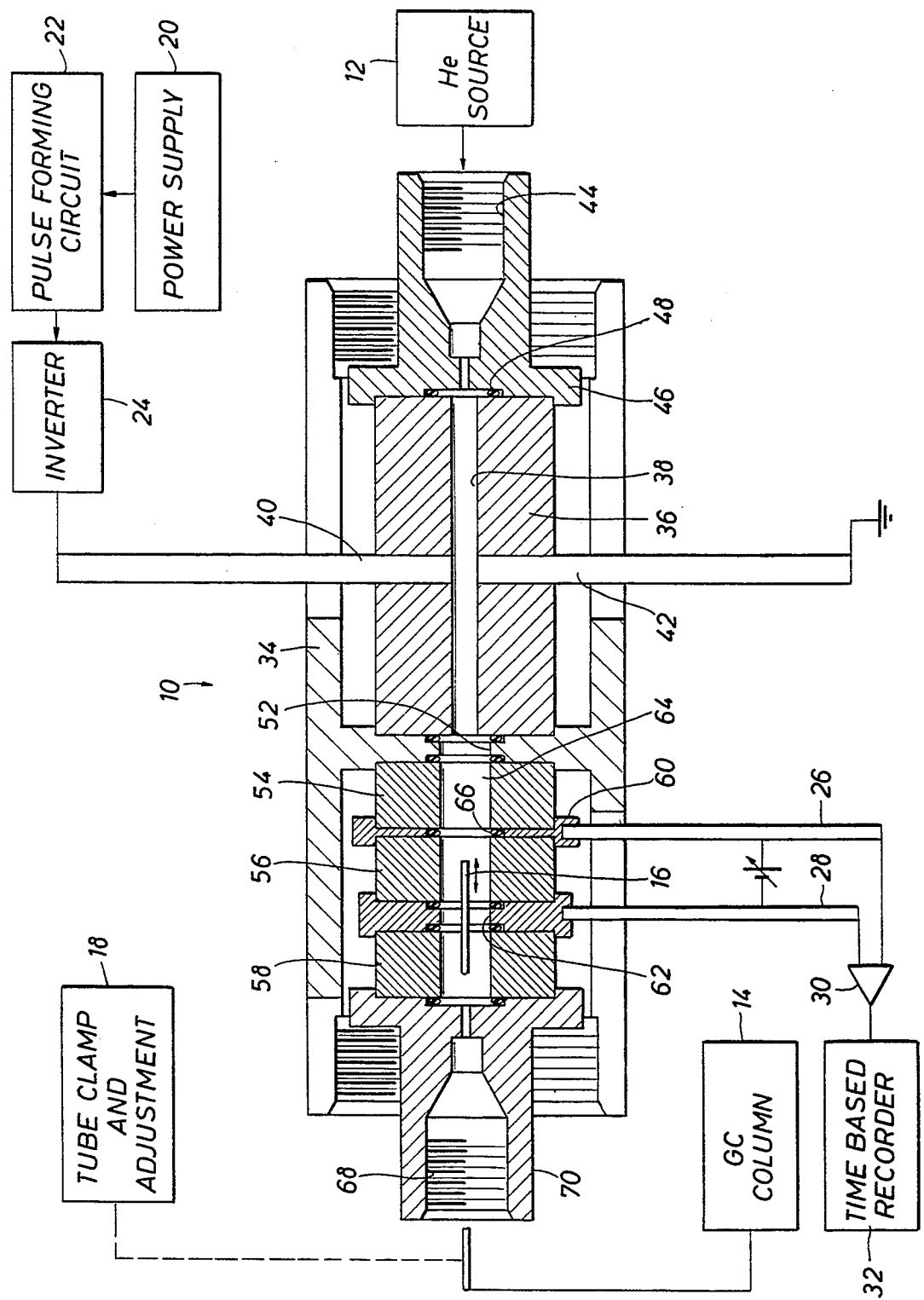

SYSTEM FOR DETECTING COMPOUNDS IN A GASEOUS SAMPLE BY MEASURING PHOTOIONIZATION AND ELECTRON CAPTURE INDUCED BY SPARK EXCITATION OF HELIUM

The present application is a continuation in part of application Ser. No. 956,632, which was filed on Oct. 5, 1992, now U.S. Pat. No. 5,317,271, which is a continuation in part of application Ser. No. 622,149, which was filed on Feb. 28, 1991, now U.S. Pat. No. 5,153,519.

BACKGROUND OF THE DISCLOSURE

The present disclosure is directed to a discharge system which forms photons which are emitted from a pulsed spark discharge. The photon spectra are primarily a broad band source of excitation. The spark interacts with a flowing helium stream to thereby provide the necessary photon emission. For this system, the apparatus utilizes a pair of spaced electrodes which provide a transverse spark across the gap between the electrodes so that the photon emission occurs.

One aspect of the present invention is the provision of a pulsed discharge system using periodically formed pulses. This enables better control of the discharge, and avoids the formation of an ionic, radiant cloud which is typical with an RF discharge system. The source is therefore discrete, fixed and finite while the RF system provides a diffused energized region. It is therefore one advantage of the present system which is uniquely able to provide the necessary ionic conversion while serving as a detector in analytical chemistry.

As mentioned in the :referenced patent above, the use of a spark discharge has advantages in that it is a different type of discharge in comparison with RF discharge. In particular, it is able to provide a discharge which is sharply defined. One aspect of this relates to the use of the present apparatus to form a spark of fixed, relatively short duration so that the exposed gas flow interacting with the spark which is held to a controlled minimum time duration. This limits the dissipation of energy from the spark. In this particular aspect, it appears that the energy discharge is primarily through photon emission. Thus the photon emission comes from a single region, a carefully defined and geometrical constrained region. A carrier gas as will be discussed is delivered through the region for interaction thereby enabling the emission of energy by means of photon discharge which interacts to provide a detector system.

One aspect of the present disclosure relates to the duty cycle. The duty cycle is relatively brief. For example, the present system can be used with a pulsed DC source to emit a narrow, sharply defined spark of relatively brief duration. This narrow spark is able to be replicated over a long interval without damaging or fatiguing the equipment. Since the equipment is primarily off because of the low duty cycle implemented, it operates at a relatively reduced temperature and is less subject to spark originated damage. The damage which typically occurs includes contact or electrode tip pitting. It also includes the unintended deposition of vaporized materials on the internal surfaces of the equipment which changes the nature of those surfaces. Those surfaces can become unintended impurity traps. By utilization of the reduced duty cycle which is set forth in this apparatus, the fatigue of the equipment is materially reduced. In one aspect of the present system the ionization system utilizes a pulsed DC spark which is applied from one electrode to another. With a brief duty cycle, the repetition rate can be in the audio frequency range. The pulses can occur as rapidly as perhaps 1000 to 2000 pulses per second. Because each pulse is separate and is relatively isolated, the pulses are able to be formed from one electrode to the other in a monopolar sequence, or they can alternately be formed in a bipolar sequence of separate monopolar pulses. This is a matter of convenience in the arrangement of the pulse forming circuitry. Thus, alternating pulses can have opposite polarity without making more complicated electronic circuitry which provides the power supply. Even though they alternate in polarity, the system nevertheless remains a DC pulse system because each pulse forms its own spark and photon discharge which is extinguished, and the following pulse is formed without interplay between consecutive pulses.

One important aspect of this system is the injection of the gas flow to be tested remote from the spark discharge. It is typically used as an output device for use with a chromatographic column, typically with a gas-chromatograph (GC) column. The output flow of the GC column includes a carrier or other solvent. A typical GC column comprises a mobile phase and a stationary phase. The mobile phase comprises a carrier gas or solvent into which sample gas containing one or more sample compounds are injected. The stationary phase comprises one or more solid constituents within the GC column which exhibit different retention times for the "unknown" sample compounds. The sample gas containing unknown compounds is injected over a relatively short period of time into the carrier gas flow near the input of the GC column. Sample compounds are retained for different times by the stationary element of the GC, and then subsequently released. Upon release, each type of sample compound is swept by the carrier gas from the GC column and discharged in the form of a "peak" or maxima in concentration in the carrier gas. Retention times, and therefore time separation of the unknown sample peaks, is a function of several factors including the carrier gas flow rate and the type of the stationary phase within the GC column. The injection, near the input of a GC column, of sample gas containing multiple compounds results in the subsequent release, or "eluates", of maxima or peak concentrations of individual compounds at the output of the GC column. The GC separates sample compounds by eluting in the form of concentration maxima or peaks in the output carrier gas at varying times, measured from the injection of the composite sample gas. As described, the GC process does not quantify the concentrations of the sample compounds, but does separate multiple compounds for further analysis using the detector disclosed herein. By using a series of calibration gases, a fixed flow rate, and a specific fixed phase material, the GC process can be used to identify compound types based upon the time position of the eluted peaks, measured with respect to the injection of the composite gaseous sample. The various peaks which are eluted through operation of the column in conjunction with the solvent or carrier may provide a sample which, in the immediate region of the spark, would form unintended soot deposits, ash or residue on the surfaces of the system. In this instance, the sample material is delivered for testing downstream of the spark but in view of the spark so that the spark is able to generate photon irradiation for the sample material delivered from the GC column or other suitable source. The output of the GC column or other test instrument is typically input into a region immediately adjacent to but offset from the spark source so that the spark does not consume the sample material in operation of the system.

Downstream from the spark source, the system utilizes first and second terminals. Two terminals are spaced on a support or mounting structure and are equipped with rings which are exposed to the downstream gas flow from the spark. The flow in this region is preferably helium which is the preferred gas introduced into the system. There is an input port for helium delivered directly through into the spark gap. Some of the helium interacts with the spark during the spark while some of the helium flows through the spark gap while no spark is being formed. The flow of helium sweeps the area, thereby directing helium flow to the two electrodes. Because helium is inert, there is no interaction from the helium flow.

The GC solvent and the eluted constituents in that flow are delivered through a relatively small, centralized, counter flow line. The flow rate of the helium is greater by perhaps 10–30 fold. The flow rate of the helium delivered into the system is able to sweep the test instrument and eluted sample flow towards the outlet. The test instrument solvent is delivered through the counter flow tube which is advanced axially in the equipment to a location to obtain optimum interaction and signal measurement. More importantly, this interacts with the flow so that the helium in the system is able to provide the necessary photon emission with relatively broad spectra thereby assuring suitable interaction of the sample material to be measured. The broad sequence spectra of the emission helps assure that the test instrument is able to see the particular sample. Otherwise, there will always be the risk that irradiation would not occur because the sample would either be transparent to the radiation or the carrier gases (helium in the preferred form) would be opaque to the emission. The ability of the helium to deliver the radiation from the broad frequency spectra is an important aspect.

It is proposed as a theory or explanation of the operation of the present system that helium introduced into the spark gap is caused to emit photons as a result of temporary formation into an unstable diatomic bond. While most gases naturally formed diatomic molecules, helium is inert which means that it has no unsatisfied valance bonds available and therefore is normally an monatomic molecule. One explanation for the phenomena obtained in this system is that the helium is excited sufficiently that a fleeting momentary bond forms molecules of diatomic helium. In breaking down to the normal monatomic form of helium, the diatomic molecule emits photons in a relatively broad energy spectra. This has been demonstrated experimentally by simply imposing a temporary shutter so that the emitted light cannot be received downstream. In the reaction area, so long as the test instrument gas discharge is irradiated with the emitted spectra, detection does occur. With the insertion of a light blocking shutter, no interaction occurs, lending proof that the reaction involves the emitted photon radiation.

In another aspect of the present system, the region between the detector electrodes at which the test instrument solvent and eluted sample materials are introduced is determined by repositioning of a moveable tube. This moveable tube is moved so that sensitivity is optimized. Moreover, the optimum sensitivity that is obtained by the system enables one to assure that tuning for a particular test instrument source can be accomplished easily. Adjustment typically occurs only with modest movement. The specific location is thus adjusted and the injection tube is then locked in place.

One further aspect of the present system is its ability to provide a relatively sensitive output signal. For a given peak amplitude input to the instrument, an output voltage peak is obtained from the system by means an electrometer. The electrometer is connected across the electrodes so that the detected current flow can be used.

Summarizing, the present apparatus is a system which utilizes a pair of spaced electrodes terminating at electrode tips or faces which are spaced across a flow path. Helium is introduced in the flow path to flow through the region. Generally, the signal is off but when a pulse is formed, the current flow from electrode face to face occurs through the helium, thereby creating the photon irradiation mentioned. A short pulse is used and the pulse is extinguished, thereby terminating further formation of photon irradiation from operation. The helium flow is directed away from the two electrodes through an elongate tubular passage which houses two exposed rings. The rings serve as first and second electrodes for an electrometer output instrument. A coaxial introduction tube is inserted from the opposite end. It discharges at the tip end of the tube any solvent and eluted flow necessary for testing. The discharge from this tube includes the solvent and eluted unknowns delivered from the test instrument. On exposure to photon irradiation generated by the spark, the specimen or sample interacts with the photon spectra thereby forming charged particles which vary the electrometer output signal.

BRIEF DESCRIPTION OF THE DRAWINGS

So that the manner in which the above recited features, advantages and objects of the present invention are obtained and can be understood in detail, more particular description of the invention, briefly summarized above, may be had by reference to the embodiments thereof which are illustrated in the appended drawing.

The single drawing is a sectional view through the helium ionization detector of the present disclosure further including the circuitry for operation and showing arrangement of the helium flow path by which helium is admitted to the spark gap and photon emission is initiated to interact with the sample input from a GC column or other source.

DETAILED DESCRIPTION OF THE PREFERRED EMBODIMENT

Attention is directed first to the single view where the pulse discharge helium ionization detector is generally identified with the numeral 10. It cooperates with certain support equipment which will be described first. Particulars of the detector 10 will then be given. The detector is provided with a flow of perhaps 20–120 milliliters per minute of helium from a helium source 12. This is delivered as a regulated flow at a pressure which is slightly above atmospheric pressure. Helium flow is from right to left in the single view and sweeps the area adjacent to the electrodes as will be described. This helium is interactive with the electrical spark described hereinafter for the purpose of defining and shaping the photon spectra emitted by the spark discharge. It is intended to cooperate with a source of sample material such as a GC column 14. The discharge effluent from the GC column 14 normally is a steady flow of a solvent or carrier which supports the flow of the eluted sample constituents. One aspect of GC column operation is that the various compounds in a sample which is input to the GC column are separated at the discharge, In other words, the GC column operates to form specific output sample, time dependent peaks depending on the nature of the constituents in the sample. Without belaboring the point excessively, the operation of the GC column is consistent with that normally intended for column operations. This means that the column output flow is primarily an established flow rate of GC effluent from its operation. The GC column 14 delivers its flow to a sample injection tube 16 which is inserted into the equipment 10 to deliver a counter flow sample at a location to be described. The sample injection tube 16 is a relatively small gauge tube which delivers the sample including the eluted peaks into the helium ionization detector 10. A tube clamp and adjustment mechanism 18 secures the tip of the sample injection tube at a desired location, and the relationship of the tube 16 to the detector will be explained in detail hereinafter. An important input to the system is obtained from a power supply 20 which provides current for operation of a pulse forming circuit 22. The pulse forming circuit connects with an inverter 24 which enables the system to output alternating positive and then negative pulses. That is input to the pair of electrodes as will be described. The system utilizes a pair of rings which provide output current flow on suitable conductors 26 and 28 which are input to a differential amplifier 30 and then to a time based recorder 32. The output signal as a function of time is recorded by the recorder 32.

The detector is constructed as a elongate cylindrical body. It incorporates a cylindrical shell 34. The shell encloses an elongate cylindrical sleeve 36 which defines a flow passage 38. Helium flows from right to left as shown, using the passage 38, and flows between the perpendicular electrodes 40 and 42. The electrodes 40 and 42 are positioned so that they have opposing faces at right angles to the passage 38. The spark which is formed across the passage 38 is preferably formed at right angles. Moreover, this intercepts the helium flow. The passage 38 is a gas flow passage, and it is also used as a light conduit to direct the illumination from the area of the spark downstream to interact with the sample as will be detailed.

The housing 34 supports an internally threaded, counter sunk, sealing shoulder fitting at 44 which enables connection with a pressure and flow regulator (not shown) which permits connection with the helium source 12. This comprises an appropriately shaped fitting and end assembly 46 which is sealed to the cylinder 36, and leakage to the exterior is prevented by the incorporation of a suitable seal ring 48. The elongate cylindrical body 36 is formed with aligned transverse passages for the electrodes 40 and 42. Moreover, the cylindrical housing 34 supports a transverse web member 50 which provides a registration surface for the cylinder 36. An axial flow path through the web 50 is observed at a central opening 52. The opening 52 aligns with an elongate cylindrical body 54 which serves as a spacer ring cooperative with similar spacer rings 56 and 58. Spacer rings 54, 56 and 58 enable easy assembly and disassembly. The spacer rings 56 and 58 connect with a circular electrode 60 which forms a full circle around the axial passage 64. This can be localized just at the surface of the passage 64 by the use of an exposed metal ring 66 which is electrically connected with the circular electrode 60. Suffice it to say, they are maintained at a common voltage because they are connected. Furthermore, they are connected so that they define a first circular terminal in the flow path. A second circular terminal is defined at the electrode 62. In this particular form of structure, the electrode 62 is thicker or wider than the dimensions of the electrodes 66. It is exposed at the axial flow passage 64 to permit the two electrodes to interact with the flowing sample mixed with the carrier gas (helium in the preferred form). That will be more clearly explained.

As mentioned, the sample tube 16 is axially inserted into the detector 10 and is moved to the left or right so that the far tip end of the moveable tube can be located. One important aspect of the present disclosure is that the tube 16 is relatively small. Its tip is located so that the tip discharge is in clear view of the region where the spark is formed between the electrodes 40 and 42. It is located in that region to assure that the discharge gas delivered from the sample tube 16 is appropriately irradiated by the light emitted from the spark. As noted earlier, this apparently is an important aspect of sample measurement because emitted light from the spark interacts to control current flow at the electrometer 30 when a clear view is maintained and yet provides no signal when a shutter is inserted to block the light transmission from the spark gap at the electrodes 40 and 42 which permits illumination of the discharge sample material from the sample tube 16. The sample tube 16 is inserted through the internally drilled fitting 68 formed in the end fitting 70. The tube clamp and adjustment device 18 is used to fasten the sample tube 16 at a specific depth of penetration. Penetration can be varied so that the tube 16 terminates at different locations. For a given test and a for specific flow rate, it is generally desirable that the end of the tube 16 be fixed at a particular location and further that the data obtained for a particular location be correlated to that location. As the tube 16 is moved to and fro, the detector 10 changes sensitivity and performance.

Going now to certain aspects of operation, one of the first things to mention is the correlation with helium flow and sample flow and location of the sample flow. As a generalization, the sample flow is typically the discharge flow rate encountered in a GC column. This typically is small, up to about 10 milliliters per minute. The carrier gas for the GC column is discharged at some rate from the tube 16. The tube 16 however confronts the flow from helium source 12 which flow is regulated at 20–120 milliliters per minute. Typically, helium flow is 6 to about 20 times greater. Therefore this larger flow rate moving from right to left sweeps the GC column discharge flow rate to the left. In other words, the GC column discharge is delivered into this passage 64 concentric with and contiguous to the passage 64 so that the sample material is swept to the left. This requires that the discharge sample flow from the tip of the sample tube 16 back to the left or concentric around the tube 16. The tube 16 is preferably formed of an inert material such as quartz. This prevents the tube 16 for interacting with the sample and other carrier materials. This assures that unwanted interactions do not occur.

The terminals 62 and 66 are provided with a bias voltage. It is preferably an adjustable bias source as illustrated. It can be changed to any desired voltage bias in order to optimize charged particle collection across electrodes 62 and 66 thereby maximize the sensitivity of the measurement. Bias voltage required to effectively collect charged particles generated under conditions of high gas flow rates and relatively poor separation of the eluted sample peaks will be different from bias voltages required for efficient charged particle collection under conditions of low gas flow rates and large separation of the eluted peaks. As will be understood, adjustment of the bias voltage may also change the current flow between the two electrodes. More will be noted concerning the source of that current flow. That relates in part to the operation of the system. System operation particular by as a helium ionization detector involves the steady flow of helium through the system from right to left as mentioned. When the spark is formed, photon emission from the spark region interacts downstream or to the left as shown in the single drawing. As the peaks defined by the GC column operation are formed and as the peak constituent material is directed into in the detector 10, current flow is created as a result of the photon spectra emitted at the spark. It appears to be a fair and accurate statement that the system operates by forming a spark which creates a photon emission spectra of relatively broad band which in turn is directed along the passage 38 and into the passage 64. This light interacts with the sample or specimen. When interaction occurs, charged particles are either formed or neutralized depending on the nature of the sample material. This creates current flow between the two terminals or electrodes 62 and 66. Restated, the amplitude of the current flow is dependent on the nature of the solvent which is discharged from the GC column and is also dependent on the amount of discharged sample material. The interaction is dependent on the formation of the spark at the gap in the helium flow whereby light is directed along the passages 38 and 64 to the region of the tip of the sample tube 16.

Generally, the tube 16 can be moved left and right and then clamped at a particular location. This enables the operator to adjust the sensitivity and interplay between the sample tube 16 and the pair of electrodes which are in the passage 64. If the tip 16 is moved farther to the left the instrument becomes less sensitive. Loss of sensitivity results from the fact that the discharged sample material is not involved in photon ionization adequately between the two electrodes and signal sensitivity is thereby lost. If the tip is moved further to the right, peak spreading occurs due to dispersion of the induced charged particle flux as the distance between the region of sample ionization and the charge collecting electrodes is increased. This position of course depends on scale factors such as the relative flow rate from the GC column and the velocity or rate of the flow from the helium source 12 and its rate of sweeping the area between the two ring shaped electrodes 62 and 66. Generally, the initial location is to align the tip of the sample tube 16 approximately with the electrode ring 66. Adjustments from that beginning location are easily achieved.

One desirable aspect of the present system is to utilize quartz or plastic materials which have been drilled with passages as illustrated which serves as a light tunnel for light from the spark gap. The cylinder 36 is an effective light tunnel.

Typical operating conditions of the present system should be noted. For one, the helium flow is delivered slightly above atmospheric pressure. A positive pressure of perhaps 1-10 psi is sufficient. The flow rate is adjusted as mentioned to the range of about 20-120 milliliters per minute. Ideally, the flow rate is between ten and thirty times larger than the flow rate from the tube 16. The system is typically operated at ambient temperatures. No particular gain is achieved by operating the system at elevated temperatures above 100° C. In some instances, operation at an elevated temperature may be needed so that samples are kept in the volatile state. The spark of the present system is provided with a low duty cycle. For instance, a typical discharge frequency might be 1000 pulses per second. In that arrangement, the power supply 20 provides sufficient power that the pulsing forming circuit 22 forms 1000 pulses per second which are evenly spaced. Each cycle of operation thus would involves one millisecond. If the spark formed by the pulse forming circuit has a duration of between 1 and 10 microseconds, the duty cycle enables the equipment to be switched off for most of the time and switched on only for one part per thousand. The pulse forming circuit 22 preferably forms a series of pulses of adequate pulse amplitude to form the spark across the two electrodes 40 and 42. If desired, alternate pulses can be inverted. It appears that both positive and negative pulses applied across the spark gap create the necessary photon ionization which interacts with the flowing sample from the sample tube 16. In other words, no harm arises from the use of monopolar or bipolar pulses.

Each pulse that is applied to the two electrodes is preferably a simple pulse of substantially short duration with minimal ringing and wherein the quiescent condition is obtained when no current is flowing and no spark exists for the moment. The spark transferred across the two electrodes 40 and 42 interacts with the inert helium gas as mentioned to form the necessary light emission triggering operation of the detector. Seemingly, this mechanism successfully operates from monopolar or bipolar sparks created in the gap between the electrodes 40 and 42.

Preferably, the electrodes 40 and 42 terminates at facing portions so that the spark across the gap is repetitively positioned. If desired, the electrodes 40 and 42 can be bare metal or can be coated with some type of protective material. For instance, quartz can be used to imbed the electrodes 40 and 42 so that the spark that is formed in confined on the interior of a quartz cylinder. While the foregoing is directed to the preferred embodiment, the scope is determined by the claims which follow.

What is claimed is:

1. A charged particle detector comprising:
   (a) a closed chamber having an inert gas flow inlet and spaced outlet to enable gas flow therethrough;
   (b) spark forming electrodes cooperating with a pulsed DC current source thereby forming a spark sufficient to enable an electrical arc to be formed between said electrodes defining the spark thereacross, said electrodes being positioned in said chamber to form a spark gap across inert gas flow through said chamber;
   (c) spaced detector means downstream in said chamber for collection of current formed as a result of the spark across the gap wherein the inert gas flow moves toward said detector means and a current is formed indicative of eluted sample concentration introduced, from an external source, into said chamber downstream from said spark forming electrodes;

(d) a voltage source connected to said detector means to provide a controlled voltage thereto for enabling said detector means for current detection; and (e) wherein the detector means quantifies the eluted sample in said chamber by measuring said detected current.

2. The apparatuc of claim 1 wherein the inert gas is helium.

3. The apparatus of claim 1 wherein said detector means is spaced remotely from said sparking forming electrodes in said chamber.

4. The apparatus of claim 1 wherein said spark forming electrodes in cooperation with said pulsed DC current source form an incandescent current flow across said gap, and said spark forming electrodes are flush mounted in a surrounding circular ring of non conductive material to enable gas flow through the spark.

5. A method of analyzing an eluted sample compound in a carrier gas comprising the steps of:
(a) flowing the carrier gas through a chamber for exposure to a spark discharge across the chamber, said spark discharge being formed across a pair of spark forming electrodes cooperating with a pulsed DC current source; and
(b) introducing an eluted sample into said carrier gas downstream from said spark discharge and observing downstream in the chamber spark caused current flow in the chamber to analyze the concentration of said eluted sample compound flowing through the chamber by detecting changes in said current flow.

6. The method of claim 5 wherein a spark of DC current flows upstream in the chamber and the carrier gas flows away from the spark for the step of observing.

7. The method of claim 6 wherein the observation of said spark caused current flow is made from a region of the chamber not involving the spark and the current flow is measured by positioning a pair of spaced electrodes in said chamber.

8. A gas detector for identification and quantification of sample compounds, comprising:
(a) an elongated chamber having a chamber inlet at one end and an outlet at the other end, and a gas flow path between said inlet and outlet ends;
(b) means for flowing helium in said chamber;
(c) two electrodes spaced apart and located to produce current spark within said chamber and across said gas flow path and wherein spark interacts with said flowing helium thereby producing photon emissions;
(d) means for introducing sample and sample carrier gas into said chamber at a Selected location remote from the electrodes in said chamber;
(e) spaced detector means downstream in said chamber for measuring current generated by the ionization of said sample by said photon emission;

means for:
(1) identifying said sample by measuring the time at which said measured current flows following said introduction of said sample into said chamber, and
(2) quantifying said sample by measuring the magnitude of said current change; and (g) means for optimizing said current generated by the ionization of said sample by adjusting said selectable location of said sample and sample carrier gas introduction into said chamber and by adjusting the voltage applied to said spaced detector means.

9. The method of claim 8 wherein said sample and sample carrier gas are from a GC column input to said chamber at a location downstream from said electrodes.

10. The method of claim 8 wherein the helium flow picks up said sample and sample carrier gas flow and mixes therewith so that said sample causes said current to flow in proportion to sample quantity.

11. A charged particle detector comprising:
(a) a closed chamber having a helium gas flow inlet at a first end and spaced outlet at a second end to enable helium flow therethrough;
(b) spaced electrodes cooperating with a pulsed DC power supply responsive to DC current flow sufficient to enable an electrical spark to be formed between said electrodes, said electrodes being positioned to form a spark in helium flow into said chamber to thereby create photon emission;
(c) spaced detector means downstream in said chamber for collection of charged particles downstream of the spark across the gap wherein the charged particles enable a current to be formed indicative of sample gas concentration in said chamber;
(d) an inlet downstream in said chamber for controllably introducing a sample and carrier gas flow from a GC column at an selected location downstream from said spark forming electrodes so that said sample and carrier gas and said helium flow provide current for said detector means; and
(h) means for optimizing said current by adjusting said selected location for sample gas and carrier gas introduction and by adjusting voltage applied to said detector means.

* * * * *